(12) United States Patent
Catlin et al.

(10) Patent No.: US 8,920,494 B2
(45) Date of Patent: Dec. 30, 2014

(54) PLUNGERS FOR INTRAOCULAR LENS INJECTORS

(71) Applicant: Abbott Medical Optics Inc., Santa Ana, CA (US)

(72) Inventors: Scott J Catlin, Pittsford, NY (US); Theophilus Bogaert, Groningen (NL)

(73) Assignee: AMO Regional Holdings, Dublin (IE)

( * ) Notice: Subject to any disclaimer, the term of this patent is extended or adjusted under 35 U.S.C. 154(b) by 0 days.

(21) Appl. No.: 13/873,563

(22) Filed: Apr. 30, 2013

(65) Prior Publication Data

US 2014/0031832 A1    Jan. 30, 2014

Related U.S. Application Data

(62) Division of application No. 12/124,055, filed on May 20, 2008, now Pat. No. 8,439,973.

(51) Int. Cl.
*A61F 2/16* (2006.01)
(52) U.S. Cl.
CPC .............. *A61F 2/167* (2013.01); *A61F 2/1664* (2013.01)
USPC ........................................................ 623/6.12
(58) Field of Classification Search
USPC ................ 606/107, 108, 166; 623/6.11–6.13
See application file for complete search history.

(56) References Cited

U.S. PATENT DOCUMENTS

| 5,772,666 | A | * | 6/1998 | Feingold et al. ............. 606/107 |
| 6,010,510 | A | | 1/2000 | Brown et al. |
| 6,162,229 | A | | 12/2000 | Feingold et al. |
| 6,447,520 | B1 | | 9/2002 | Ott et al. |
| 2007/0005135 | A1 | | 1/2007 | Makker et al. |

OTHER PUBLICATIONS

Definition of "Flare", Retrieved from the Internet <URL: http://www.merriam-webster.com/dictionary/flare>.

* cited by examiner

*Primary Examiner* — Ashley Fishback
(74) *Attorney, Agent, or Firm* — AMO Regional Holdings (57) ABSTRACT

An intraocular lens (IOL) injector for delivering an IOL into an eye of a patient includes an IOL load chamber and connected delivery tube, and a push rod for urging the IOL through the delivery tube and out of a distal tip thereof. The push rod is guided and biased against one side of the injector load chamber. The injector may include an inflatable pusher for urging the IOL through the delivery tube and out of a distal tip thereof. The inflatable pusher has a proximal end that may be open to an internal cavity of the injector, wherein a plunger movable in the injector cavity forces fluid such as air or saline into the pusher. A distal end of the pusher may be forked to capture a trailing end of the IOL, or may have a bulbous configuration to ensure the pusher does not pass the IOL.

18 Claims, 10 Drawing Sheets

PLUNGERS FOR INTRAOCULAR LENS INJECTORS

CROSS-REFERENCE TO RELATED APPLICATIONS

This application is a divisional application and claims priority to U.S. application Ser. No. 12/124,055, entitled "Plungers For Intraocular Lens Injectors", filed on May 20, 2008, the entire contents of which are hereby incorporated by reference in its entirety for all purposes as if fully set forth herein.

FIELD OF THE INVENTION

The present invention relates to systems and methods for delivering an intraocular lens (IOL) into an eye through an injector/cartridge and, more particularly, to plungers for urging an IOL through an injector/cartridge.

BACKGROUND OF THE INVENTION

It is estimated that 73% of Americans between the ages of 65 to 74 get cataracts. A cataract is a clouding of the eye's lens that impairs a person's vision and, if left untreated, causes blindness. As a result, each year approximately 1.4 million people in the United States alone undergo cataract surgery, whereby the clouded natural crystalline lens is removed and replaced with an intraocular lens (IOL) implant.

Surgeons implant IOLs not only as a replacement for the natural crystalline lens but also to alter the optical properties of (provide vision correction to) an eye in which the natural lens remains. IOLs often include an optically clear disk-like optic of about 6 mm in diameter, and preferably at least one flexible fixation member or haptic which extends radially outward from the optic and becomes affixed in the eye to secure the lens in position. Implantation of such IOLs into the eye involves making an incision through the cornea. It is advantageous, to reduce trauma and increase the speed of healing, to have an incision size as small as possible.

The optics may be constructed of rigid biocompatible materials such as polymethyl methacrylate (PMMA) or deformable materials such as silicone polymeric materials, acrylic polymeric materials, hydrogel polymeric materials, and the like. The deformable materials allow the IOL to be rolled or folded for insertion through an injector or insertion cartridge and an incision into the eye. Once within the chamber of the eye, the IOL is expulsed from the injector and returns to its original shape. The primary deformable IOL materials are silicone and acrylic (hydrophobic and hydrophilic). Silicone IOLs are in general more pliable and can be folded into smaller tubes without unduly stressing the insertion cartridge or requiring excessive push force, which can suddenly expel the IOL from the cartridge. Acrylic lenses are inserted in much the same way as silicone IOLs, although in general using larger bore cartridges to mitigate the problems caused by the typically lower flexibility of the acrylic. Because the cartridge bore is larger, the incision is also necessarily larger, though some acrylics are implanted through micro incisions (<2 mm).

Injectors for delivering IOLs into the eye typically employ a handpiece and a removable cartridge that receives the IOL and has a hollow insertion tube or cannula through which the folded IOL is passed using a push rod. Some injectors do without the cartridge and are reusable. The IOL is stored separately and transferred to a load chamber in the injector or cartridge just prior to delivery. One particularly useful arrangement wherein the cartridge folds over an IOL is disclosed in U.S. Pat. No. 4,681,102 to Bartell. A cartridge opens to receive an IOL in a load chamber, and then folds closed and fits into an injector. A syringe-like plunger in the injector pushes the IOL from the load chamber through a tapered tube into the eye. The IOL unfolds as it emerges from the tip of the tapered tube. Another such insertion system is disclosed in Makker et al., U.S. Pat. No. 5,942,277.

The goal of achieving safer cataract surgery and reduced patient recovery time has resulted in smaller and smaller incisions, often less than 3 mm. Because the tip diameter of the injector or cartridge must be reduced accordingly, the IOL must likewise assume a smaller profile as it passes into the eye. This increases the force required to push the IOL through the small cartridge lumen, and impacts on the dynamics between the plunger and the IOL. Even with the introduction of a viscoelastic medium therebetween, the forces required to push the IOL against friction through the cartridge sometimes result in the push rod riding over the IOL, pinning one of the haptics against the inner lumen of the cartridge, or damaging to the trailing edge of the IOL.

Moreover, the IOL is deformable so the point where it is engaged may shift if the push rod does not have sufficient lateral stiffness. Likewise, the deformed shape of the IOL may result in a reaction force on the plunger with a force component in a lateral direction that displaces the push rod, causing it to bypass the IOL. Although one solution is to stiffen the push rod by increasing its cross-section, and reducing its length, these are not practical modifications as they run counter to the desire for a small and often elongated cartridge lumen.

One attempt to maintain contact between a plunger and IOL is seen in U.S. Pat. No. 5,494,484 to Feingold, which discloses a plunger having a faceted tip configured to engage the trailing edge of the IOL optic. U.S. Pat. No. 6,010,510 to Brown, et al. includes an injector having a plunger with an offset tip. The tip flexes up onto the floor of the cartridge so that there is a constant downward bias and the tip does not ride over the IOL. U.S. Pat. No. 6,558,395 to Hjertman discloses an insertion system with an elastic plunger capable of being reshaped, and having a guiding groove in the floor of the cartridge for stabilizing and centering the plunger. Also, U.S. Pat. No. 6,093,193 and U.S. Patent Publication No. 2007-0005135, both to Makker, et al., disclose push rods having soft tips.

Despite a number of advances in this field, there remains a need for a more gentle IOL insertion system that reduces the chance of a push rod or plunger from damaging, bypassing or otherwise riding over an IOL as it proceeds through small cartridge lumens.

SUMMARY OF THE INVENTION

One aspect of the present invention is a plunger for an IOL injector that can flex elastically, vertically and/or laterally, and is guided both vertically and laterally under controlled pre-tension. Because of this, the plunger position can be accurately controlled in that the pre-tension keeps the plunger pressed against the guides independent of slight misalignments arising from the manufacturing or assembly processes. As a result, tolerances can be widened and lateral play between the plunger and its guides are eliminated by the pre-tension.

In accordance with one aspect, a system for delivering an intraocular lens (IOL) into the eye of a subject, comprises an IOL injector defining a load chamber for receiving an IOL. A delivery tube communicates with the load chamber and terminates at a distal tip. The injector further includes a push rod movable through the load chamber for urging the IOL in a distal direction from the load chamber, through the delivery tube and out of the distal tip in a delivery procedure. A guide within the injector exerts a camming force on the push rod to transversely urge the push rod in one or more directions. The load chamber is preferably adapted to receive an IOL in an orientation such that an axis of the IOL optic defines a vertical plane, wherein the camming force acts laterally on the push rod. In one embodiment, the guide comprises a V-shaped slot. The guide may extend linearly in the direction of travel of the push rod, or otherwise, such as in a spiral path.

Another aspect of the invention is a system for delivering an intraocular lens (IOL) into the eye of a subject comprising an IOL injector defining a load chamber for receiving an IOL. A delivery tube communicates with the load chamber and terminates at a distal tip. The injector further includes a push rod movable through the load chamber for urging the IOL in a distal direction from the load chamber, through the delivery tube and out of the distal tip in a delivery procedure. The push rod translates along an axis that is angled with respect to the load chamber axis so as to cause a distal end of the push rod to contact the load chamber and create a compressive bias therebetween. A guide within the injector may exert a force on the push rod in a different plane than the plane in which the compressive bias is created.

The guide may also exert a lateral force on the push rod. In one embodiment, the guide comprises a V-shaped slot. The guide may extend linearly in the direction of travel of the push rod, or otherwise, such as in a spiral or winding path. The distal end of the push rod desirably features a protrusion that contacts the load chamber proximal from a distal-most extent of the distal end. In one embodiment, a groove within the injector receives a distal end of the push rod and against which the push rod is compressively biased. If the push rod features a protrusion, it may contact the groove within the injector. In one form, the groove abruptly terminates at a distal end so as to limit distal movement of the push rod.

In accordance with a further aspect, the present invention provides an IOL injector system for delivering an intraocular lens (IOL) into the eye of a subject. The system includes an IOL injector defining a load chamber for receiving an IOL and a delivery tube in communication with the load chamber and terminating at a distal tip. An inflatable pusher within the injector has a proximal end and a distal end, the distal end being sized to extend substantially through the injector to the distal tip when the pusher is inflated. A plunger having a piston is movable within the injector and adapted to force fluid into and inflate the pusher when moving in a first direction. Desirably, the piston is movable within the injector toward and away from the proximal end of the inflatable pusher, the piston adapted to force fluid into and inflate the pusher when moving toward the proximal end thereof. For instance, the plunger may move longitudinally through the injector in a syringe-like manner.

In accordance with one embodiment, the inflatable pusher has a forked distal end, or may have a bulbous distal end. The inflatable pusher preferably has an open proximal end sealed within a cavity of the injector, and the plunger moves within the cavity to force fluid into the proximal end. The fluid may be incompressible, such as saline, or compressible such as air. The system further may include a cartridge that defines the load chamber and which mates with the injector.

Another aspect of the invention is an inflatable pusher adapted to be used with an injector for urging an intraocular lens (IOL) into the eye of a subject. The pusher has an open proximal end and a distal end, the distal end being adapted to extend when the pusher is inflated. The pusher may have a forked distal end, or a bulbous distal end. In one form, the pusher has a bellows configuration.

The present invention also provides a method of injecting an intraocular lens (IOL) into the eye of a subject. The method includes providing an IOL injector defining a load chamber and a delivery tube in communication with the load chamber and terminating at a distal tip, a plunger, and an inflatable pusher having a proximal end and a distal end, the distal end being sized to extend substantially through the injector to the distal tip when the pusher is inflated. An IOL is placed into the load chamber of the injector, and the plunger is actuated to force fluid into and inflate the pusher. Preferably, the plunger is movable within the injector toward and away from the proximal end of the inflatable pusher, and is adapted to force fluid into and inflate the pusher when moving toward the proximal end thereof. In one embodiment, the plunger moves longitudinally through the injector in a syringe-like manner. The fluid may be incompressible, such as saline, or compressible such as air. A cartridge may be provided that defines the load chamber and which mates with the injector, and wherein the step of placing the IOL into the load chamber is followed by mating the cartridge with the injector.

The present invention also provides a method of injecting an intraocular lens (IOL) into the eye of a subject. The method includes providing an IOL injector defining a load chamber and a delivery tube in communication with the load chamber and terminating at a distal tip, a plunger, and an inflatable pusher having a proximal end and a distal end, the distal end being sized to extend substantially through the injector to the distal tip when the pusher is inflated. An IOL is placed into the load chamber of the injector, and the plunger is actuated to force fluid into and inflate the pusher. Preferably, the plunger is movable within the injector toward and away from the proximal end of the inflatable pusher, and is adapted to force fluid into and inflate the pusher when moving toward the proximal end thereof. In one embodiment, the plunger moves longitudinally through the injector in a syringe-like manner. The fluid may be incompressible, such as saline, or compressible such as air. A cartridge may be provided that defines the load chamber and which mates with the injector, and wherein the step of placing the IOL into the load chamber is followed by mating the cartridge with the injector.

BRIEF DESCRIPTION OF THE DRAWINGS

Embodiments of the present invention will be better understood from the following detailed description when read in conjunction with the accompanying drawings. Such embodiments, which are for illustrative purposes only, depict the novel and non-obvious aspects of the invention. The drawings include the following figures, with like numerals generally indicating like parts.

DETAILED DESCRIPTION OF THE PREFERRED EMBODIMENTS

The present invention facilitates the process of delivering an intraocular lens (IOL) into a patient's eye using an injector. The IOL is typically implanted using an injector that rolls, folds, or otherwise configures the lens for delivery through a small incision in the eye in a way that reduces trauma and expedites post-surgery healing. The IOL is stored separately and transferred to an injector or cartridge just prior to delivery. The injector or injector/cartridge is used in a manner like a hypodermic needle with the IOL being injected into the eye through a delivery tube. The injector, cartridge and/or delivery tube are first partially filled with a liquid or gel lubricating agent, for example a viscoelastic material.

Figure 1:
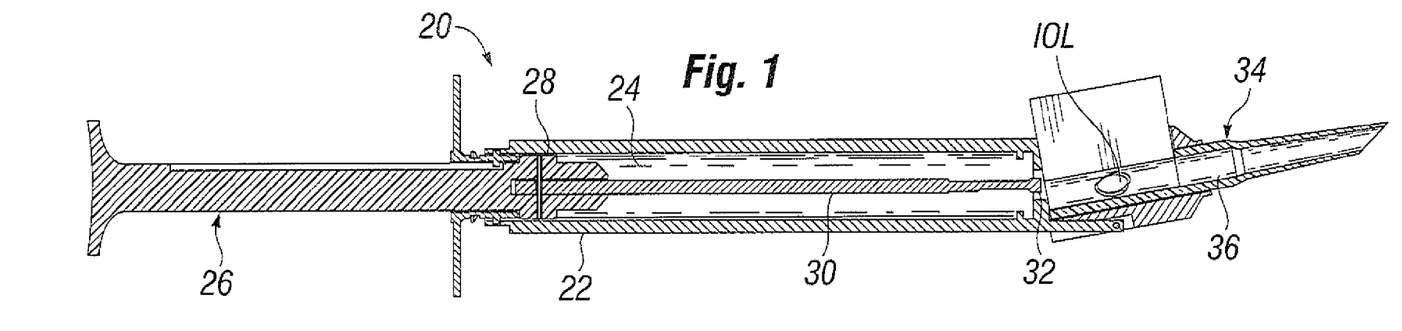
FIG. 1 is a sectional view of an exemplary insertion system according to an embodiment of the invention where a plunger advances at a slight angle to the cartridge lumen.

FIG. 1 is a longitudinal sectional view of an insertion system 20 according to an embodiment of the invention. The insertion system 20 comprises an injector 22 defining and inner bore 24 within which reciprocates a plunger 26 having a piston 28 on the distal end that seals against the bore 24. The main portion of the injector 22 is sometimes termed a handpiece, and in the illustrated embodiment resembles a syringe with a tubular main body that receives the plunger 26. The piston 28 interacts with a push rod 30 having a distal end 32 that extends through the inner bore 24.

The injector 22 receives a cartridge 34 on a distal end thereof. The cartridge encloses an IOL and defines a lumen 36 leading to a distal delivery tip 38. An opening in the injector 22 enables the push rod 30 to extend through the cartridge lumen 36 upon depression of the plunger 26. The cartridge 34 is oriented at a slight angle with respect to the longitudinal axis of the injector 22. In this manner, the distal end 32 of the push rod 30 contacts a lower floor of the cartridge lumen 36 shortly after entering the cartridge. It should again be stated that the present invention is also applicable to systems where the loading and delivery area are integrated into a hand piece of an injector in a so-called preloaded system.

Figure 2:
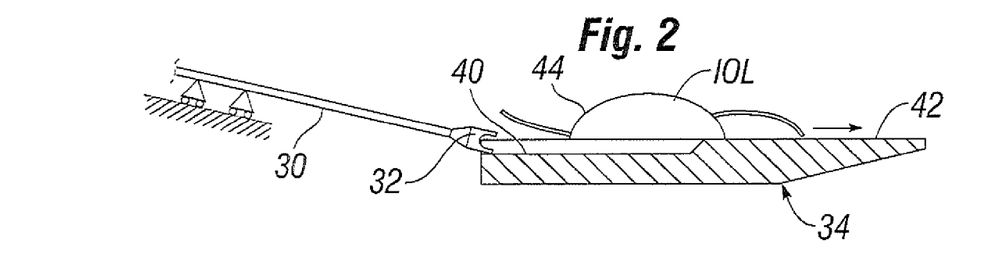
FIG. 2 is a schematic diagram of the insertion system of FIG. 1.

FIG. 2 is a schematic diagram of the insertion system 20 of FIG. 1, and illustrates travel of the push rod 32 toward the IOL. The cartridge 34 is shown having a lower groove 40 within which the distal end 32 of the push rod 30 is guided. The IOL rests on a floor 42 of the cartridge 34 such that it is suspended over the groove 40. The distal end 32 of the push rod 30 may be forked or otherwise shaped to capture a trailing edge 44 of the IOL. The push rod 30 is rigidly connected to the piston 28 (FIG. 1) and can only move linearly along its own axis. Desirably, the push rod 30 is made from a flexible material, such as polypropylene. Because of the angle at which the push rod 30 enters the cartridge and contacts the groove 40, the push rod 30 flexes and the distal end 32 exerts a downward force on the groove. This pre-tension in the push rod 30 helps maintain contact with the cartridge lumen and prevent the distal end 32 from riding over the IOL.

The angle of movement of the push rod 30 with respect to the cartridge lumen 36 is desirably about 10°. The groove 40 is desirably wider than the distal end 32 at its proximal end (to the left in FIG. 2), and gradually narrows toward the distal end (to the right) to a width that is slightly larger than the distal end, preferably about 0.1 mm larger. The distal end 32 is therefore guided by the groove 40 toward the center of the cartridge 34. The groove may have a rectangular cross-section with vertical sidewalls, in which case the pre-tension is only vertical, imparted by the bottom floor of the groove. Alternatively, the groove 40 may have a V-shaped, chevron-shaped, or U-shaped cross-section which will impart lateral contact and guidance to the push rod distal end 32. As the push rod 30 and distal end 32 moves distally through the cartridge 34, the bending stress in the push rod increases because of the angle at which the push rod travels. The increase bending stress represents an increase in the force holding the distal end 32 against the inner wall of the cartridge lumen 36, which is desirable because as the distal end 32 advances through the cartridge the reaction force from the IOL increases also. That is, the cartridge lumen 36 gradually narrows in the distal direction in a funnel-like manner, and more force is required to push the IOL therethrough. After the distal end 32 reaches the end of the groove 40, it continues through the cartridge 34 guided by the narrow lumen 36.

Figure 3:
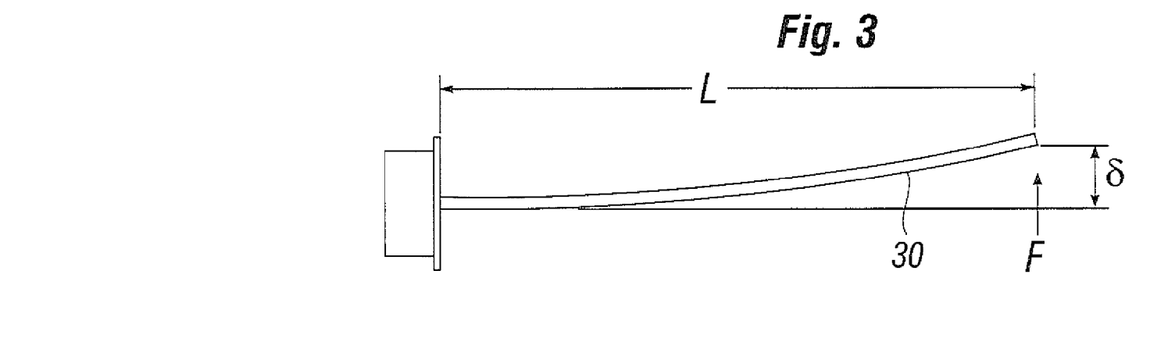
FIG. 3 is a force diagram of the plunger of the system in FIG. 2.

FIG. 3 is a force diagram of the plunger of the system in FIG. 2. The push rod 30 is idealized has a simple beam having a length L, and the reaction force from the cartridge lumen 36 is indicated by the upper force arrow F. If the push rod 30 has a height h and base width b, the area moment of inertia is given as:

$$I = bh^3/12$$

The pre-tension force F in a vertical plane is then translated as:

$$F = 3E \cdot I \cdot \delta / L^3$$

where E is the Young's modulus and δ is the deflection of the distal end 32.

In this regard, the distal end 32 deflects a lateral distance δ that equates to the displacement thereof due to contact with the inner wall (e.g., floor) of the cartridge lumen 36 from a point where it would end up if permitted to advance linearly. If the cartridge floor is uneven, the push rod 30 will flex nonlinearly. For example, if a groove 40 is provided as in FIG. 2, the system may be designed such that the push rod 30 does not experience bending, and pre-tension, until the distal end 32 rides up onto the cartridge floor 42. Likewise, if the push rod 30 advances nonlinearly it will flex in a nonlinear fashion. In all of these situations, the pre-tension will maintain contact between the distal end 32 and the cartridge lumen 36. If, in being urged through the cartridge, the IOL exerts a force on the distal end 32 that is perpendicular to the cartridge and away from the floor of the cartridge, the distal end remains in contact with the cartridge lumen unless the pre-tension force is exceeded. Preferably, the system is designed such that the magnitude of deflection, δ, is 1 mm or larger so that the pre-tension is relatively robust.

In one particular embodiment, the push rod 30 is made of a flexible material such as polypropylene or another suitable polymer. The push rod 30 is rigidly connected to a sliding fixation point that can only move in an axial direction (idealized as a guiding carriage in FIG. 2). The push rod 30 is prevented from rotating about its axis. The length of the push rod 30 is about 50 mm, and the structure is such that a force F of about 0.5 N is required to deflect the distal end 32 laterally 4.3 mm. As mentioned, the push rod 30 desirably advances at an angle of about 10° with respect to the axis of the cartridge lumen 36. Initially, the distal end 32 is not in contact with the cartridge lumen 36, and desirably contacts the lumen within about 25 mm of travel before reaching the cartridge distal tip 38 (see FIG. 1).

In various embodiments, the groove 40 may have a rectangular, rounded, V-shaped, or other cross-section. If rectangular, and wider than the distal end 32, the only channeling force applied to the distal end is vertical. However, if the groove 40 is V-shaped, for example, one or two lateral components of force are also applied to the distal end 32. In the latter case, the push rod 30 experiences a pre-tension that both maintains it in contact with the groove and also guides it along a particular path. If the groove 40 is linear, the path is linear. However, in some instances it may be desirable to cause the distal end 32 to translate laterally, in which case the groove 40 can be angled, serpentine, or some other configuration. For instance, if rotation of the IOL around the axis of the cartridge 36 is desired, the groove 40 may curve or spiral around the lumen of the cartridge to cause such IOL rotation.

Figure 4:
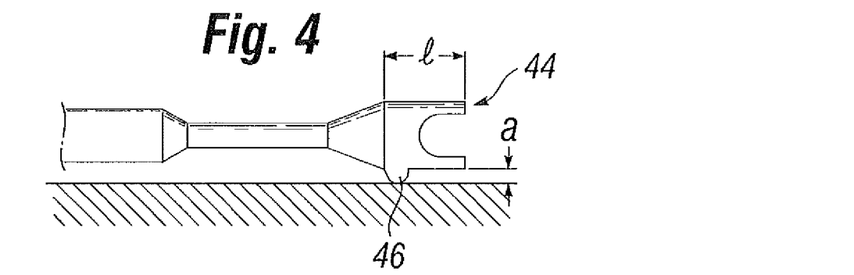
FIG. 4 is a side elevational view of a distal end of a plunger of the present invention having a feature on its bottom surface that interacts with the bottom surface of the loading chamber of an inserter.

FIG. 4 is a side elevational view of a distal end 44 of a plunger or push rod of the present invention having a feature on the bottom surface that interacts with an inserter. Depending on the cartridge material and coating, it may be desirable that the distal-most point of the plunger (or push rod) does not contact the cartridge wall. In some instances, the distal end can scrape or remove material (e.g., a coating) from the cartridge lumen, which can then be transferred to the IOL, creating a problem after implant. To elevate the distal end 44 the plunger or push rod includes a feature on its lower surface close to the distal end 44 that projects downward and contacts the cartridge lumen. In FIG. 4, a bump or protrusion 46 projects downward from the distal end 44 so as to contact the cartridge floor and maintain a gap a of, for example, 0.1 mm therebetween. The protrusion 46 is set back from the distal-most point of the distal end 44 by a distance l, which may vary depending on the angle between the push rod and the cartridge and the size of the protrusion.

Desirably, the groove 40 blends gradually to the cartridge floor 42 to avoid causing any discontinuity or jamming of movement of the push rod 30. However, in some instances a more abrupt ending to the groove 40 may be preferable. For instance, if the protrusion 46 on the push rod distal end 44 seen in FIG. 4 travels in a groove, forward motion of the push rod may be halted by interference between the protrusion and a suddenly ending groove. This may be desirable if distal movement of the push rod must be stopped at a particular point.

Figure 4A:
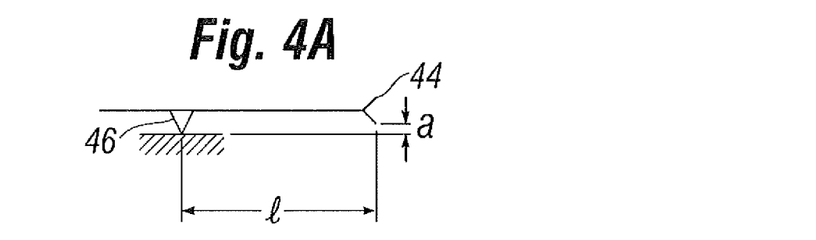
FIGS. 4A-4E are schematic diagrams showing several possible geometric relationships between plungers and insertion cartridges.

FIGS. 4A-4E are schematic diagrams showing several possible geometric relationships between plungers and insertion cartridges utilizing the protrusion 46. The protrusion 46 makes contact with the cartridge wall (e.g., floor) which can be maintained with a constant or vertical force by means of the pre-tension described above. As seen in FIG. 4A, the gap a between the distal end 44 and the cartridge floor will be maintained where the pusher and cartridge floor run parallel. If the distance l between the protrusion 46 and the distal tip of the distal end 44 is 10-20 mm, overlap of the protrusion with any IOL elements such as optic or haptics is prevented. Conversely, if the protrusion 46 is within 10 mm, the distal end 44 will be guided with somewhat more stability.

Figure 4B:
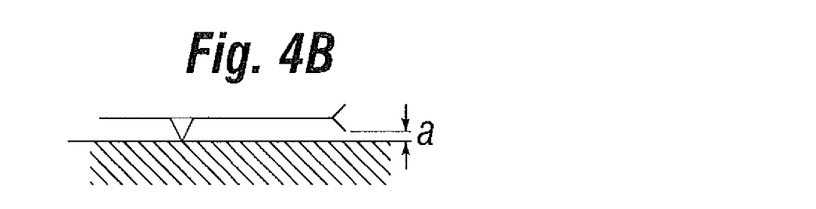
Figure 4C:
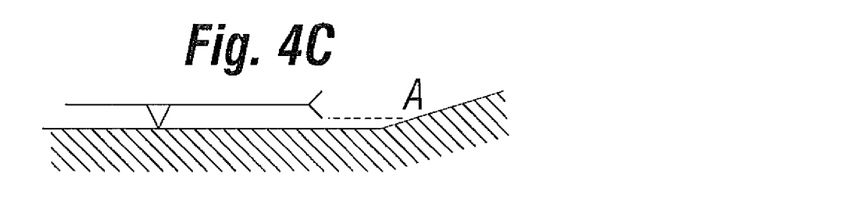
Figure 4D:
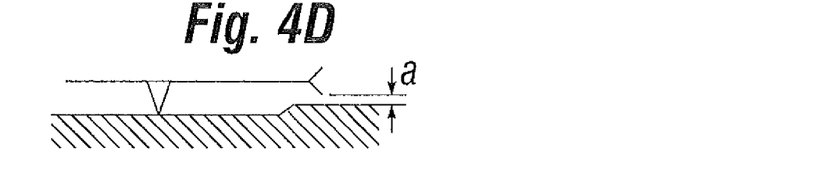
Figure 4E:
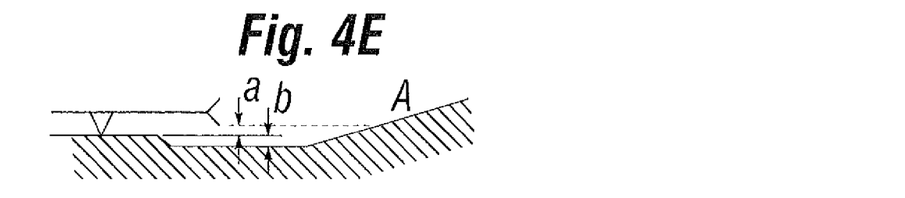

In FIG. 4B, the push rod advances in parallel to the cartridge floor and the protrusion 46 maintains the gap a between the distal end 44 and the cartridge wall. In FIG. 4C, the floor of the cartridge is shown angled upward such that the distal end 44 contacts it at point A. Up to that point, the protrusion 46 maintains the gap a. In FIG. 4D the protrusion 46 may travel within a groove that is recessed below that portion of the cartridge wall over which the distal end 44 travels. Again, the protrusion 46 maintains a gap a between the distal end 44 and the cartridge floor. Finally, FIG. 4E illustrates a cartridge having both an incline and a groove. The gap between the distal end 44 and the cartridge wall may be varied by causing the protrusion 46 to travel first on the cartridge floor then within a groove. Initially, the gap is shown as the sum of a+b, but after the protrusion 46 enters the groove the gap is reduced to just a. These alternatives, schematically shown, illustrate basic options for cartridge/injector systems in accordance with the present invention.

Figure 5:
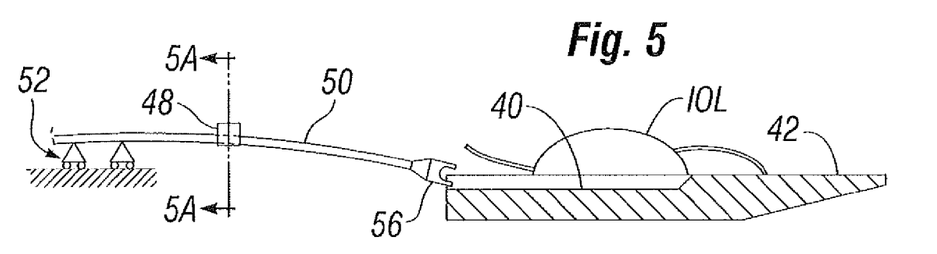
FIG. 5 is a schematic diagram of an alternative insertion system which utilizes an upper guide that acts to bias a plunger downward.
Figure 5A:
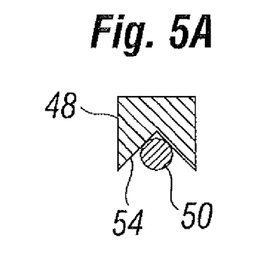
FIG. 5A is a cross-section of an exemplary V-shaped guide that may be used in the system of FIG. 5.

FIG. 5 is a schematic diagram of an alternative insertion system which utilizes an upper guide 48 to bias a plunger or push rod 50 downward. Again, the push rod 50 translates linearly along an idealized carriage 52. The guide 48 contacts and deflects the push rod 50 downward. As seen in an exemplary cross-section in FIG. 5A the guide 40 may have a V-shaped groove 54 within which the push rod 50 translates. The groove 54 therefore exerts lateral forces on the push rod 50 and can maintain its centricity, or may be utilized to deflect the push rod laterally.

The distal end 56 of the push rod 50 translates within the cartridge lumen and ultimately contacts the IOL. In the illustrated embodiment, the cartridge has a groove 40 within which the distal end 56 initially translates and a floor 42 on which the IOL rests. Desirably, at the moment the distal end 56 contacts the IOL optic, it still has lateral and vertical freedom of movement. In a preferred embodiment, the cross-section of the push rod 50 is such that it more easily flexes horizontally than vertically. For example, the height of the push rod 50 may be larger than its width. At the moment of engaging the IOL, the push rod 50 is allowed to align itself because of this freedom of movement. Subsequently, as the push rod 50 advances, urging the IOL distally, the distal end 56 deflects downward under the influence of the upper guide 48 and is compressively biased against the groove 40. This adds stiffness and stability.

Figure 6A:
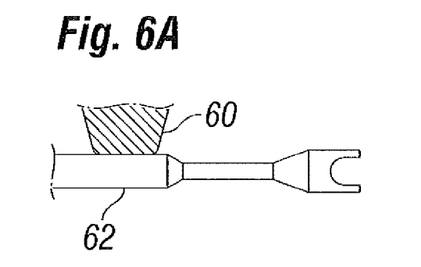
FIGS. 6A, 6B and 6C are cross-sections of alternative guides that may be used to bias plungers of the present invention.
Figure 6B:
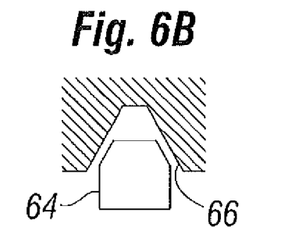
Figure 6C:
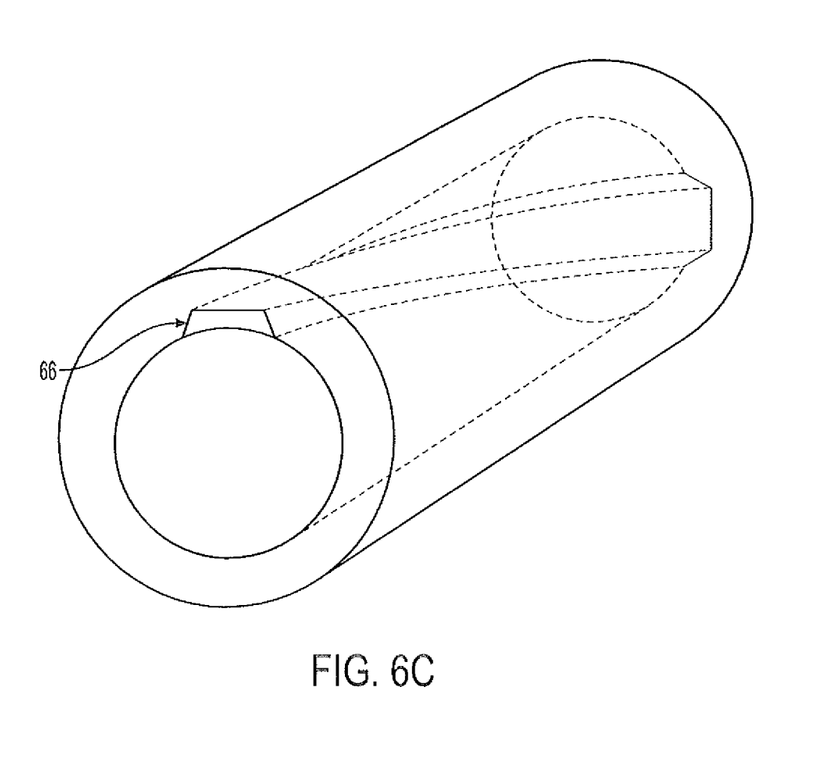

FIGS. 6A and 6B are cross-sections of alternative guides that may be used to bias plungers/push rods of the present invention. In FIG. 6A, a blunt guide 60 contacts one side of the push rod 62. The guide 60 has a flat face that merely exerts a lateral force on the push rod 62, rather than guiding along more than one axis. The guide 60 may be positioned above the push rod 62, as shown, or on either left or right side so as to bias the push rod in the opposite direction. In FIG. 6B, a push rod 64 has chamfered upper corners that conform to a truncated V-shaped groove 66. The groove 66 channels the push rod 64, but the matching shapes and truncation help prevent any binding therebetween. Again, the groove 66 may be formed in a spiral path, for example, to induce rotational movement to the push rod 64, as seen in FIG. 6C.

Figure 7A:
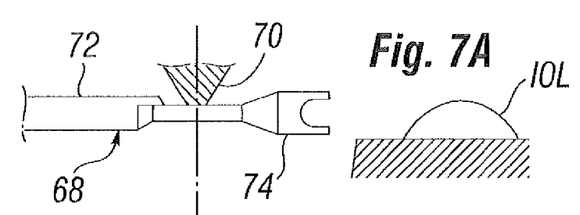
FIGS. 7A and 7B are schematic views of an alternative mechanism for biasing an insertion plunger having an uneven cross-section.
Figure 7B:
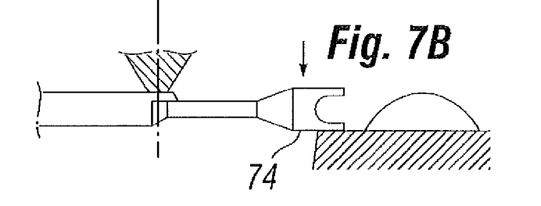

FIGS. 7A and 7B are schematic views of an alternative mechanism for biasing an insertion plunger having an uneven cross-section. The first portion of a push rod 68 is initially in contact with a guide 70. A distal movement of the push rod 68 causes a second raised portion 72 thereon to contact the guide 70. In this manner, the distal end 74 is forced downward and into contact with the cartridge floor so as to prevent riding over the IOL. This cam action between the push rod 68 and the guide 70 can be accomplished by an uneven push rod, or an uneven guide 70.

Figure 8:
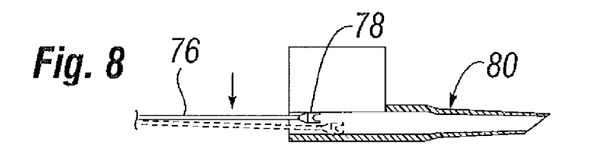
FIGS. 8, 9, 10A, 10B, 11A, 11B, and 11C are schematic views of still Further alternative mechanisms for biasing an insertion plunger.
Figure 9:
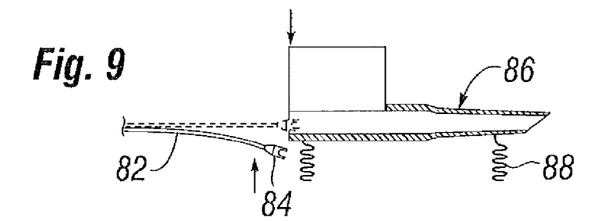
Figure 10A:
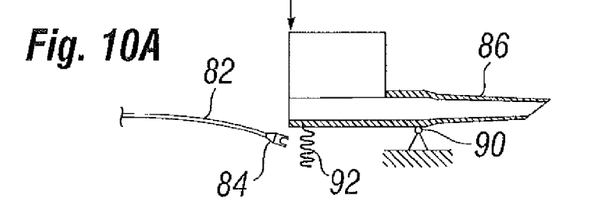
Figure 10B:
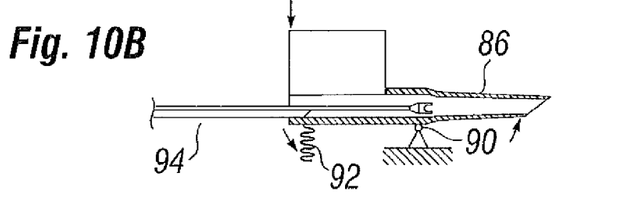
Figure 11A:
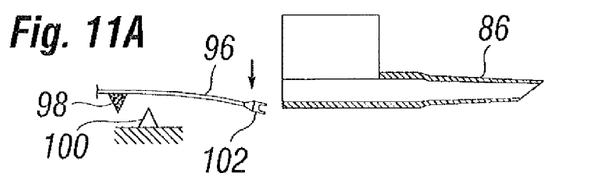
Figure 11B:
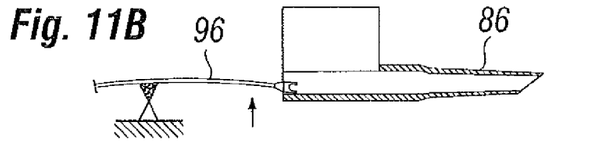
Figure 11C:
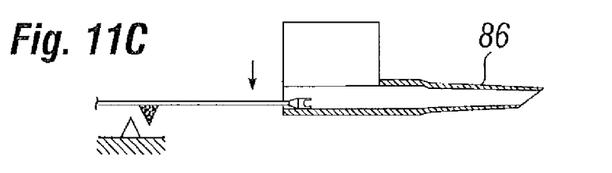

FIGS. 8-11 are schematic views of still further alternative mechanisms for biasing an insertion plunger. In FIG. 8, a straight push rod 76 is pressed down after a distal end 78 enters a lumen of a cartridge 80. In this regard, a moving guide may be utilized, such as one which is triggered by linear movement of the push rod 76. In FIG. 9, a curved push rod 82 has a distal end 84 that is lifted just prior to entering a lumen of the cartridge 86. Alternatively, the cartridge may be depressed as indicated by the downward arrow, and may be biased upward by a spring force, schematically shown as two springs 88. FIGS. 10A and 10B are similar to FIG. 9, but the cartridge 86 pivots about hinge point 90 and is biased upward at its rear end by only one spring 92. The curved push rod 82 enters the lumen after depressing the rear end of the cartridge 86, which is then released to create a compressive bias between the distal end 84 and the lumen of the cartridge 86. After advancing within the lumen of the cartridge 86 such that the distal end 84 passes the hinge point 90, a thicker region or cam 94 on the push rod 82 contacts the cartridge lumen and maintains a downward pressure thereto. This helps maintain a compressive bias between the distal end 84 and the lumen of the cartridge 86. Finally, FIGS. 11A-11C illustrates a curved push rod 96 having a protrusion 98 thereon. Interference between the protrusion 98 and a guide 100 associated with the injector or the cartridge lifts the distal end 102 so that it enters the lumen of the cartridge 86. Once in the cartridge 86, the protrusion 98 passes the guide 100, allowing the curved push rod 96 to exert a downward force on the cartridge lumen, and the bias or pre-tension is established.

Figure 12A:
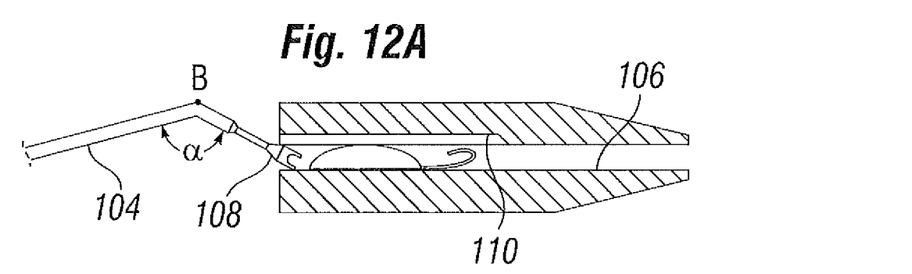
FIGS. 12A-12C are sectional views of a still further aspect of the present invention including a non-linear plunger that interacts with the cartridge lumen to bias the plunger.
Figure 12B:
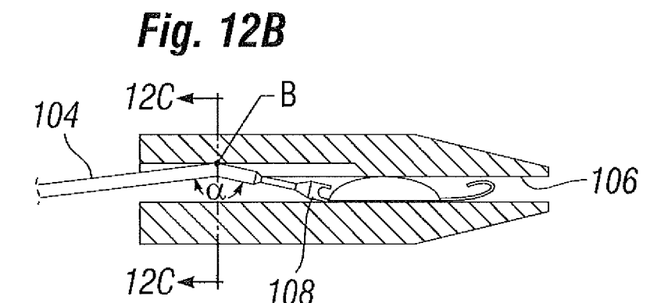
Figure 12C:
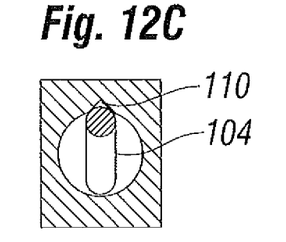

FIGS. 12A-12C are sectional views of a still further aspect of the present invention including a non-linear plunger 104 that interacts with a cartridge lumen 106 to bias the plunger against the lumen. More specifically, the plunger 104 in its unstressed condition has a curved or, as illustrated, angled configuration, which is bent at an angle α at a point B. A distal portion terminating in the distal end 108 is directed downward. When the plunger 104 enters the cartridge lumen 106, uppermost point B enters a groove 110 in the ceiling of the lumen. The plunger 104 is thus guided by the groove 110, and straightens out by virtue of simultaneous contact between the distal end 108 and floor of the cartridge lumen 106 (i.e., the angle α increases). The elastic deformation of the plunger 104 creates a vertical downward force that the distal end 108 exerts on the floor of the cartridge lumen 106. Again, lateral forces exerted on the plunger 104 by the guide groove 110 maintains the plunger centered within the lumen.

Figure 13A:
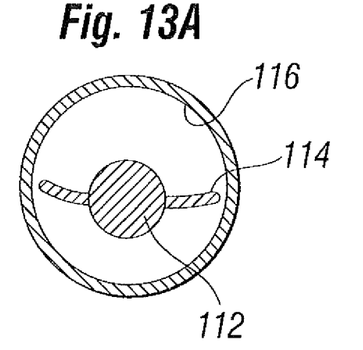
FIGS. 13A and 13B are sectional views of an alternative pusher rod tip with deformable wings.
Figure 13B:
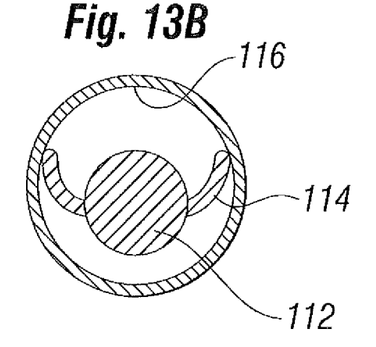

FIGS. 13A and 13C are sectional views of an alternative pusher rod tip 112 with deformable wings 114. The rod tip 112 is seen in a relaxed state in FIG. 13A and after having been advanced through an injector lumen 116 in FIG. 13B. As the lumen 116 gets smaller, the wings 114 will deform, thus biasing the rod tip 112 and adding stiffness to the system. More precisely, the wings 114 tend to curl up to conform to the shape of the injector lumen 116, and in doing so push the central portion of the rod tip 112 in one direction, for instance to the bottom of the lumen as shown.

In addition to biasing and guiding push rods/plungers, the present invention may also incorporate an extensible member that helps prevent binding of the IOLs. A push rod that is guided for an initial portion of its travel may also incorporate an extensible member to finish pushing the IOL the last portion. Variations of extensible members are shown and described below, and it should be understood that the various embodiments may be combined with the several push rod embodiments described above.

Figure 14A:
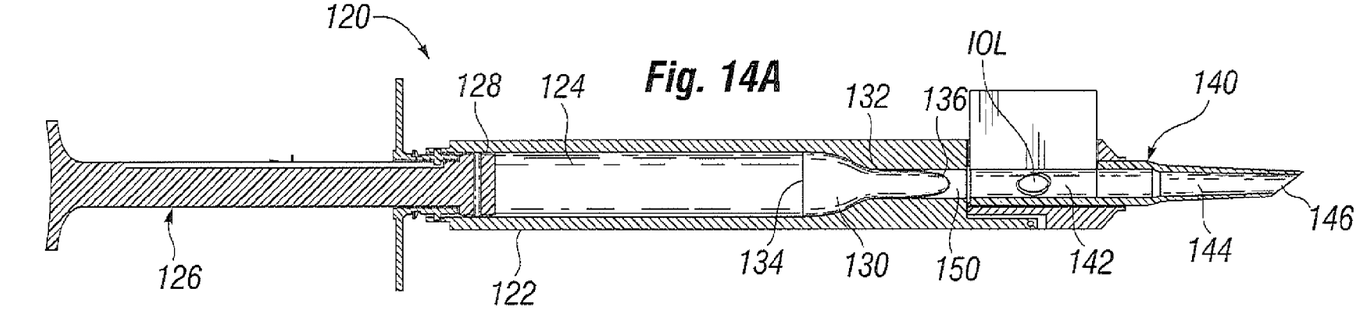
FIG. 14A is a partial longitudinal sectional view of an exemplary intraocular lens (IOL) insertion system according to an embodiment of the invention having an extensible pusher for urging an IOL therethrough.

FIG. 14A is a partial longitudinal sectional view of an insertion system 120 according to another embodiment of the invention. The insertion system 120 comprises an injector 122 defining an inner bore 124 within which a plunger 126 reciprocates. The main portion of the injector 122 is sometimes termed a handpiece, and in the illustrated embodiment resembles a syringe with a tubular main body that receives the plunger 126 having a piston 128 on the distal end that seals against the bore 124.

An extensible pusher 130 is positioned at the distal end of the bore 124. The pusher 130 includes an extensible distal portion 132 and an open proximal end 134. The distal portion 132 terminates at a distal end 136, which in the illustrated embodiment is rounded. In a preferred embodiment, the extensible pusher 130 comprises an inflatable balloon formed of a material that permits significant elongation. For example, the pusher 130 may be formed of thin-walled silicone rubber. In a preferred embodiment, the distal end of the injector 122 defines a funnel shape which mirrors the relaxed shape of the extensible pusher 130.

In the insertion system 120 axial movement of the plunger 126 translates into axial movement of the extensible pusher 130. One benefit may be that a predetermined displacement of the plunger 126 may be converted to greater displacement of the pusher tip, or visa versa. If the former, the axial dimension of the injector can be reduced.

The distal end of the injector 122 includes a cavity that closely receives an IOL injector cartridge 140. As mentioned above, some insertion systems do without the cartridge and thus the term injector for those encompasses certain structural aspects associated with the illustrated cartridge. The cartridge 140 defines a load chamber 142 within which is shown in IOL. It through bore within the cartridge 140 leads to a delivery channel 144 and the distal opening 146. As is known in the art, the IOL can be urged through the cartridge 140 and from the distal opening 146 into the eye of a patient.

Figure 14B:
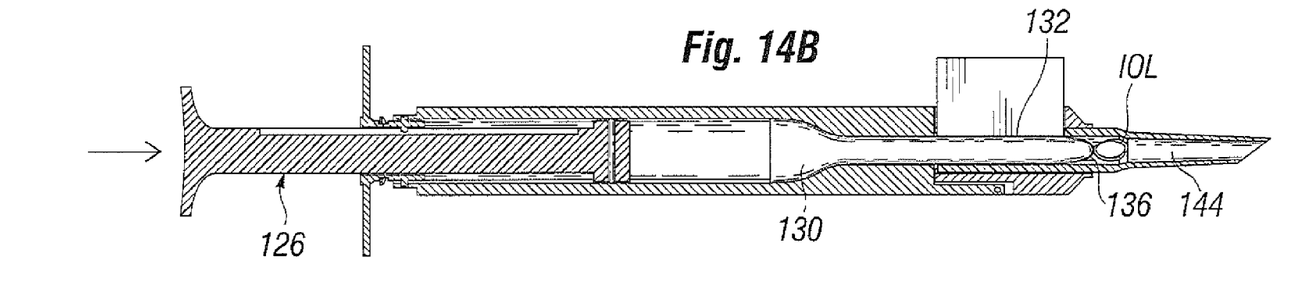
FIGS. 14B and 14C are partial longitudinal sectional views of the system of FIG. 14A showing two stages of advancement of a plunger to force fluid into the extensible pusher.
Figure 14C:
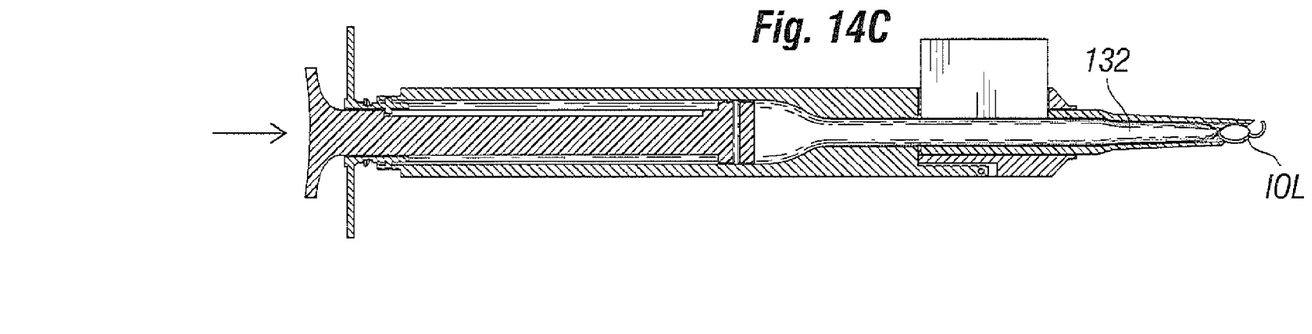

With reference to FIGS. 14B and 14C, an operator depresses plunger 126 with his or her fingers to cause the piston 120 to translate distally within the injector bore 124. As the plunger 126 advances, the piston 128 forces fluid within the bore 124 into the open end 134 of the extensible pusher 130. As a result, the extensible distal portion 132 elongates such that the distal tip 136 passes through an opening 150 and into the load chamber 142 of the cartridge 140. Further advancement of the plunger 126 displaces the distal end 136 into contact with the IOL, thus urging the IOL through the cartridge 140. The flexible nature of the pusher material helps prevent damage to the IOL in comparison to a rigid pusher rod.

The working fluid provided within the bore 124 of the injector 122 may be incompressible, such as the saline or a viscoelastic medium, or compressible such as air or nitrogen. Desirably, the extensible pusher 130 is constructed with a significant safety factor so as to ensure no ruptures occur. For instance, the extensible pusher 130 can be formed with limited elasticity. However, small openings in the distal end 136 may permit a controlled release of a small amount of the working fluid, such as a viscoelastic medium. In the absence of such openings, one or both of the pusher 130 and cartridge lumen are desirably coated with a lubricious substance such as a viscoelastic medium to reduce friction and promote smooth extension of the inflating pusher. Further, an inflation pre-load may be provided such that the extensible pusher 130 is partly inflated, or at least is inflated to a point just before the distal portion 132 begins stretching. This reduces the required amount of travel of the plunger 126.

Although a syringe-like injector 122 having a linearly movable plunger 126 is shown, other ways for forcing fluid into an extensible pusher are contemplated. Any actuator having a piston movable within the injector bore adapted to force fluid into and inflate the pusher when moving in a first direction may be used. For example, instead of being linearly depressed, the plunger 126 may be rotated so as to translate axially, thus increasing the sensitivity of the extension of the pusher 130. Likewise, the linearly movable pusher 126 may be replaced with a trigger-like actuator or lever which moves the piston 128. Those of skill in the art will understand that the invention is not limited by the illustrated syringe embodiment.

Similarly, the pusher 130 shown as a funnel-like balloon having an open proximal end 134. However, it may be necessary to provide some type of rigid support or flange at the proximal end 134 to prevent the pusher from moving distally through the injector. In this regard, the term open proximal end with reference to the end 134 encompasses variations that include an opening to the bore 124 that permits fluid to travel from the bore to the interior of the pusher 130.

Figure 15A:
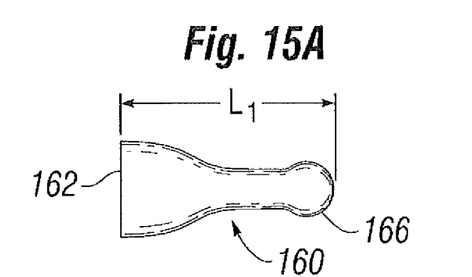
FIGS. 15A and 15B are elevational views of an alternative extensible pusher of the present invention having a bulbous distal end shown in refracted and extended configurations.
Figure 15B:
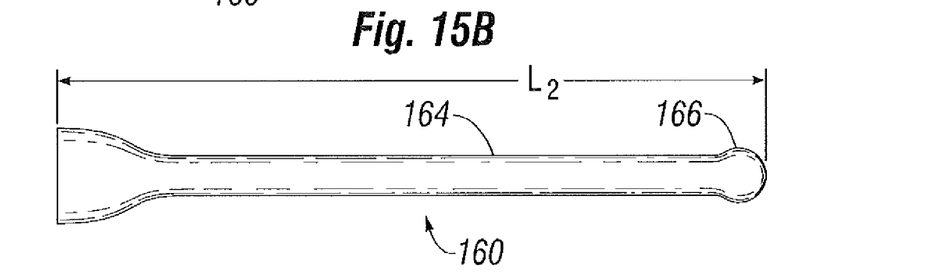

Now with reference to FIGS. 15A and 15B, an alternative pusher 160 is shown in retracted and extended configurations, respectively. The pusher 160 again includes an open proximal end 162 and an extensible distal portion 164 terminating in a distal end 166. Rather than being rounded or tapered, as in the first embodiment, the distal end 166 is slightly enlarged from the remainder of the distal portion 164 so as to form a bulbous end. Various shapes of balloons can be formed for use as the extensible pusher 160, such as the bulbous end shown, or one which has a flat distal face. Such a configuration helps ensure that the pusher successfully urges the IOL from the cartridge, and prevents the IOL from becoming wedged between the pusher and the inner lumen of the cartridge.

FIGS. 15A and 15B also illustrate the change in length between the retracted configuration $L_1$ and the extended configuration $L_2$. In a preferred embodiment, the pusher 160 is made a silicone rubber having a high elongation factor such that $L_2/L_1$ is at least 2, and more preferably about 4. Of course, the lengths to which the pusher 160 must extend depends on its positioned relative to the loaded IOL a, and the length of the injector or cartridge delivery tip. Those of skill in the art will understand that a variety of different extensible pushers are suitable for the present invention.

Figure 16:
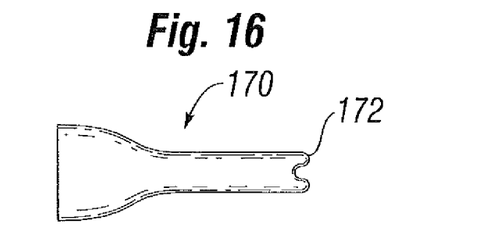
FIG. 16 is an elevational view of an alternative extensible pusher having a forked distal end.

In an alternative embodiment shown in FIG. 16, an extensible pusher 170 has a forked distal end 172. A forked shape is sometimes used in rigid injector rods to capture a trailing end of the IOL optic. Because of the flexible/inflatable nature of the pusher 170, the forked distal end 172 helps prevent damage to sometimes delicate IOLs. A forked end 172 also enables rotational manipulation of the IOL. In the latter instance, a means of rotating the pusher 170 may be included.

Figure 17A:
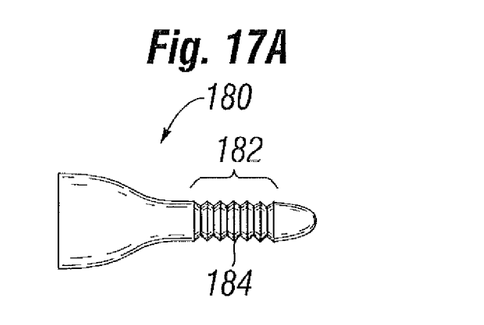
FIGS. 17A and 17B are elevational views of a further alternative extensible pusher of the present invention having a bellows structure shown in retracted and extended configurations.
Figure 17B:
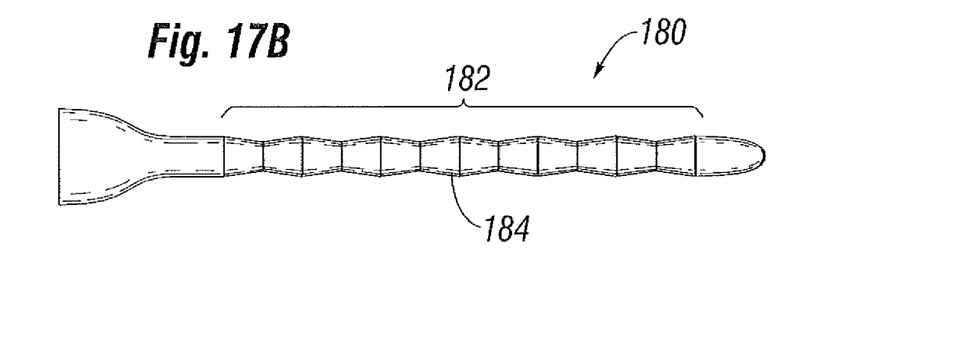
Figure 18:
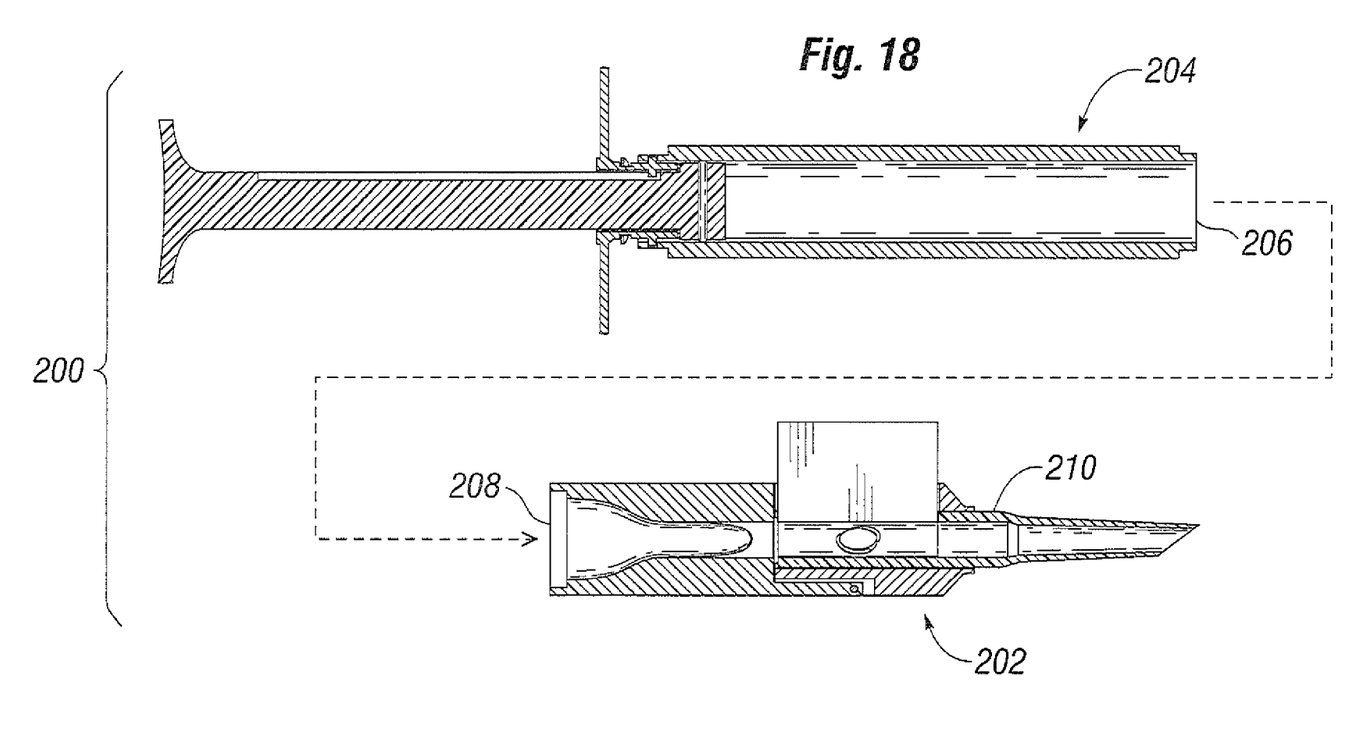
FIG. 18 is an exploded view of an alternative injector system with a disposable cartridge and pusher subassembly that mates with a reusable handpiece.

FIGS. 17A and 17B illustrate a still further alternative extensible pusher 180 having a bellows configuration. In particular, the pusher 180 includes a mid-section 182 having pleats or folds 184. In this construction, the material used for the wall of the pusher need not be quite as extensible, merely flexible. Of course, there are other configurations similar to a bellows designed, such as a balloon having a middle section that has been folded upon itself FIG. 18 shows exploded an alternative injector system 200 with a disposable cartridge and pusher subassembly 202 that mates with a reusable handpiece 204. A male end 206 of the handpiece 204 fluidly seals against a female end 208 of the subassembly 202. The various working parts of the system are as described above. A cartridge 210 may be separable from the subassembly 202 as shown and described above, or may be incorporated therein. A surgeon selects an IOL and loads it into the cartridge 210, then mates the subassembly 202 with the handpiece 204 and injects the IOL as before.

The present invention thus provides an improved pusher for urging an IOL through an injector or cartridge that is more gentle to the IOL. For that matter, the distal end of the various pusher described herein may be capped with a very soft material to further enhance the gentle handling of the IOL.

Figure 19A:
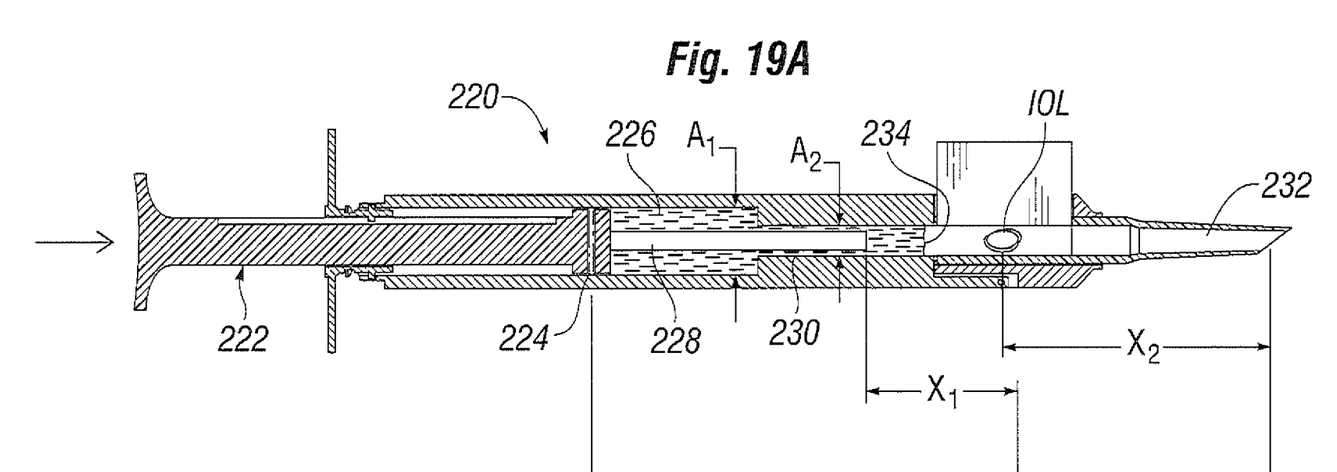
FIGS. 19A and 19B are longitudinal sectional views of an alternative intraocular lens (IOL) insertion system that utilizes a hydraulic pusher.
Figure 19B:
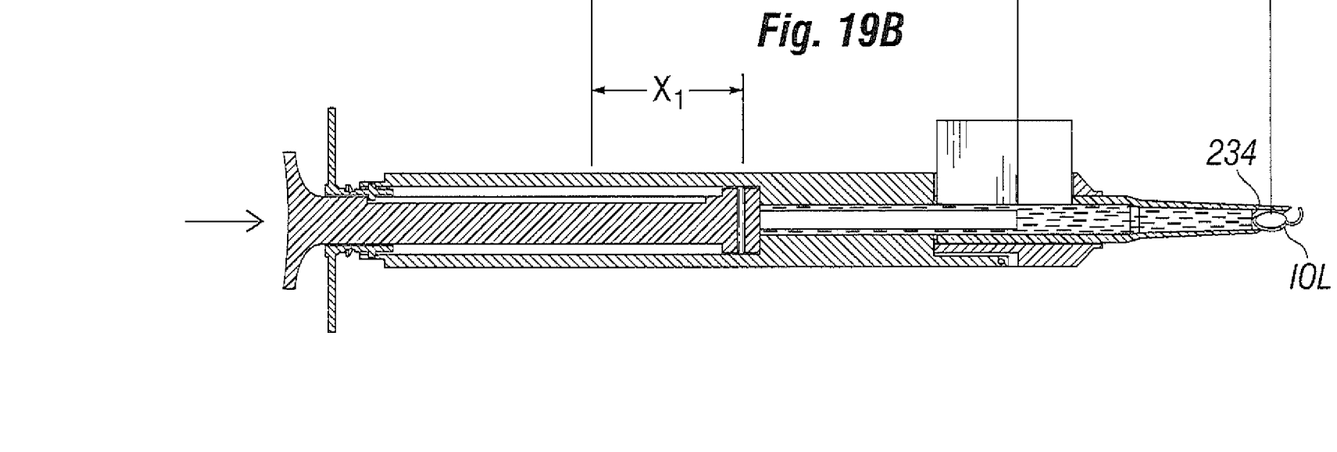

In a still further embodiment, FIGS. 19A and 19B illustrate an alternative intraocular lens (IOL) insertion system 220 that utilizes a hydraulic pusher. Specifically, a plunger 222 having a seal 224 reciprocates within a chamber of an injector 226. A distal rod 228 extends within a smaller lumen 230 leading to a cartridge lumen 232 (or an extension of the injector handpiece in unitary systems). A hydraulic front 234 of fluid within the chamber will urge the IOL forward more rapidly than a solid plunger tip because of the difference in cross-sections $A_1$ and $A_2$. That is, the plunger 222 and rod 228 translate a distance $x_1$, while at the same time the IOL travels a longer distance $x_2$. The fluid is desirably a viscous biocompatible fluid such as a viscoelastic medium (e.g., Healon). If the fluid leaks around the IOL the tip of the distal rod 228 physically impels the IOL forward.

It is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A system for delivering an intraocular lens (IOL) into the eye of a subject, comprising:
    an IOL injector defining a load chamber for receiving an IOL and a delivery tube in communication with the load chamber and terminating at a distal tip;
    an inflatable pusher within the injector comprising a balloon that has a proximal end and a distal end, the distal end being sized to extend substantially through the injector to the distal tip when the pusher is inflated; and
    a plunger having a piston movable within the injector and adapted to force fluid into and inflate the pusher when moving in a first direction.

2. The system of claim 1, wherein the piston is movable within the injector toward and away from the proximal end of the inflatable pusher, the piston adapted to force fluid into and inflate the pusher when moving toward the proximal end thereof.

3. The system of claim 2, wherein the plunger moves longitudinally through the injector in a syringe-like manner.

4. The system of claim 2, wherein the inflatable pusher has a forked distal end.

5. The system of claim 2, wherein the inflatable pusher has a bulbous distal end.

6. The system of claim 2, wherein the inflatable pusher has an open proximal end sealed within a cavity of the injector, and the plunger moves within the cavity to force fluid into the proximal end.

7. The system of claim 2, wherein the fluid is incompressible.

8. The system of claim 2, wherein the fluid is saline.

9. The system of claim 2, wherein the fluid is compressible.

10. The system of claim 2, further including a cartridge that defines the load chamber and which mates with the injector.

11. The system of claim 10, wherein the cartridge and pusher are provided in a disposable subassembly that mates with a handpiece of the injector.

12. A method of injecting an intraocular lens (IOL) into the eye of a subject, comprising:
providing an IOL injector defining a load chamber and a delivery tube in communication with the load chamber and terminating at a distal tip, a plunger, and an inflatable pusher within the injector comprising a balloon having a proximal end and a distal end, the distal end being sized to extend substantially through the injector to the distal tip when the pusher is inflated; and
placing an IOL into the load chamber of the injector;
actuating the plunger to force fluid into and inflate the pusher.

13. The method of claim 12, wherein the plunger is movable within the injector toward and away from the proximal end of the inflatable pusher, the plunger adapted to force fluid into and inflate the pusher when moving toward the proximal end thereof.

14. The method of claim 13, wherein the plunger moves longitudinally through the injector in a syringe-like manner.

15. The method of claim 12, wherein the fluid is incompressible.

16. The method of claim 15, wherein the fluid is saline.

17. The method of claim 12, wherein the fluid is air.

18. The method of claim 12, further including a cartridge that defines the load chamber and which mates with the injector, and wherein the step of placing the IOL into the load chamber is followed by mating the cartridge with the injector.

* * * * *